United States Patent [19]

Haber

[11] Patent Number: 4,709,690

[45] Date of Patent: Dec. 1, 1987

[54] IMPLANTABLE BLOOD FLOW AND OCCLUSION PRESSURE SENSING SPHINCTERIC SYSTEM

[75] Inventor: Terry M. Haber, Lake Forest, Calif.

[73] Assignee: Habley Medical Technology Corporation, Laguna Hills, Calif.

[21] Appl. No.: 853,963

[22] Filed: Apr. 21, 1986

[51] Int. Cl.$^4$ .................................................. A61F 1/00
[52] U.S. Cl. .................................... 128/1 R; 128/346; 128/DIG. 25; 623/14
[58] Field of Search ............... 128/DIG. 25, 346, 1 R, 128/686, 734, 642, 326, 325, 327; 623/14

[56] References Cited

U.S. PATENT DOCUMENTS

| | | | |
|---|---|---|---|
| 4,256,094 | 3/1981 | Kapp et al. | 128/DIG. 25 X |
| 4,399,809 | 8/1983 | Baro et al. | 128/DIG. 25 X |
| 4,408,597 | 10/1983 | Tenney | 128/DIG. 25 X |

Primary Examiner—Michael H. Thaler
Attorney, Agent, or Firm—Morland C. Fischer

[57] ABSTRACT

An implantable, percutaneously accessed blood flow and occlusion pressure sensing sphincteric system including an inflatable occlusion cuff to surround a patient's urethra for occluding and relaxing the urethra to produce lumenal coaptation for the treatment of urinary incontinence. The occlusion cuff is electro-fluidically interconnected to a hyponometer by way of electro-fluidic coupling, a coaxial, electrically conductive hypodermic needle, and a fluid pressure regulating and control chamber. Thus, the occlusion cuff can be percutaneously and variably infused with a precisely measured supply of fluid from the hyponometer for inflating the cuff and thereby increasing the application of occlusive pressure to the urethra. The occlusion cuff is provided with a transducing element, so that the patient's arteriovascular blood pulses through the urethra can be remotely monitored at the hyponometer to enable the physician to receive a visual and/or audible indication when blood flow through the patient's urethra is compromised as a consequence of applying excessive occlusive pressure to the urethra. Hence, the risks of ischemia and necrosis, as an undesirable result of overpressurizing the occlusion cuff, can be minimized.

25 Claims, 5 Drawing Figures

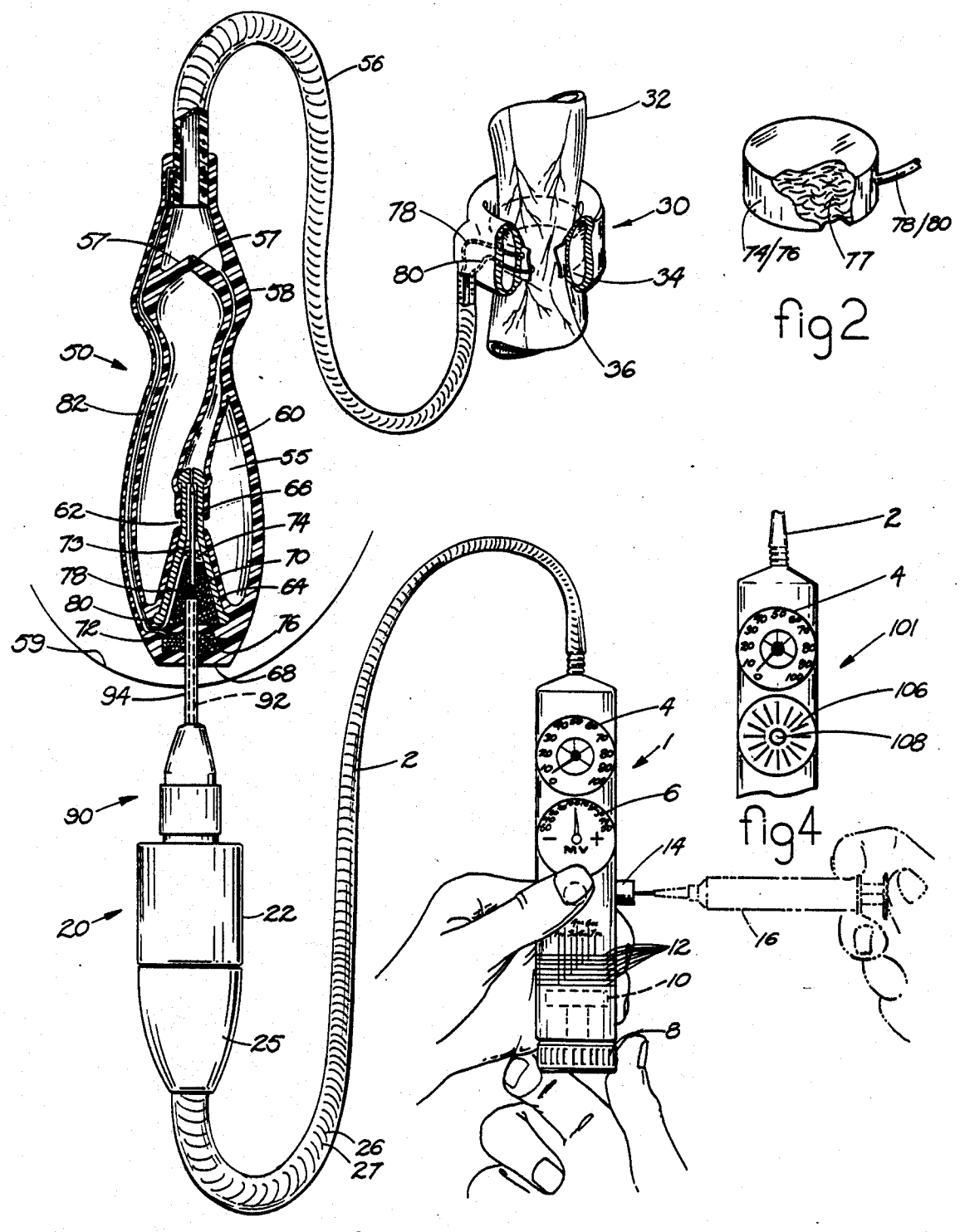

IMPLANTABLE BLOOD FLOW AND OCCLUSION PRESSURE SENSING SPHINCTERIC SYSTEM

BACKGROUND OF THE INVENTION

1. Field of the Invention

This invention relates to an implantable, sphincteric system to overcome urinary incontinence. An occlusion cuff is electro-fluidically interconnected to a hyponometer so that the cuff can be percutaneously infused with and inflated by a measured supply of fluid from the hyponometer to increase or decrease the application of occlusive pressure to the patient's urethra at the same time that the patient's blood flow through the urethra is being monitored to prevent over-inflation of the cuff and the generation of excessive occlusive pressure which could undesirably compromise lumenal blood flow.

2. Prior Art

As will be recognized by those skilled in the art, certain individuals, because of a disability or surgical procedure or other organic and/or psychogenic cause, do not possess adequate function or competence of various bodily organs or muscles so as to achieve natural sphincteric continence for controlling the involuntary passage of urine. Accordingly, many sphincteric mechanisms have been proposed for surgical implantation as part of a system to selectively occlude and relax a lumen, such as the urethra, for controlling the passage of material therethrough. However, most known sphincteric mechanisms are characterized by a common shortcoming. That is, once the implant surgery is completed, there is no readily available means (without necessitating additional surgery) to accurately and continuously adjust the sphincteric pressure to be applied to the urethra, or other lumen, to achieve continence.

More particularly, because of the swollen and aggravated condition of edema of the urethral tissues during and for a period subsequent to surgery, the physician cannot be certain as to the normalized condition of the patient's urethra until post-operative edema has subsided. Therefore, the physician must estimate the required minimal occlusive pressure needed to produce continence. As a consequence of such estimate, sphincteric mechanisms are often improperly fitted or selected, so that the maximum occlusive pressure capability of such mechanism is insufficient to successfully achieve continence or the minimum occlusive pressure capability exceeds the pressure needed to achieve continence and preserve blood flow. Excessive occlusive pressure is known to undesirably minimize arteriovascular blood flow to the urethra and thereby increase the possibility of ischemia, necrosis and erosion to the delicate urethral tissues.

Moreover, where conventional sphincteric mechanisms include occlusive force control means, such force control is usually accomplished in large, step-wise increments. Therefore, few artificial sphincters are known which are adapted to easily and accurately control, or continuously vary, the occlusive pressure needed to achieve continence, so that the sphincter may be percutaneously adjusted by a physician to the individual needs of the patient on an ongoing basis without requiring additional surgery. What is more, no sphincteric mechanisms are known which include the electro-fluidic interconnection between an occlusion-producing cuff and a hyponometer, so that the patient's blood flow through the urethra can be accurately monitored by the physician to prevent the application of excessive occlusive pressure to the urethra which could compromise such blood flow.

SUMMARY OF THE INVENTION

Briefly, and in general terms, a blood flow and occlusion pressure sensing sphincter system is disclosed for surgical implantation to treat urinary incontinence. The sphincter system includes a hollow, inflatable occlusion cuff which is positioned around a patient's urethra to generate sufficient occlusive pressure to produce continence. The occlusion cuff is electro-fluidically interconnected to a hyponometer by way of an electro-fluidic coupling, an electrically conductive hypodermic needle, and an occlusion pressure regulating and fluid control chamber. Thus, a fluid path is established between the occlusion cuff and the hyponometer, such that fluid infusion and expulsion can be controlled by the physician to inflate the cuff and adjust the maximum occlusive pressure level to the urethra. The patient may manually manipulate the pressure regulating and control chamber at a palpable, loose skin area (at the posterior superior aspect of the scrotum) to transfer fluid from a fluid filled reservoir of the chamber into the occlusion cuff to inflate the cuff. In the event that the occlusive pressure is insufficient to produce continence, the physician may percutaneously and variably infuse the cuff with an accurately measured supply of fluid from the hyponometer to further inflate the cuff and increase the maximum occlusive pressure level to the urethra until continence is produced. Hence, the physician may selectively set the maximum occlusive pressure level applied to the urethra without subjecting the patient to additional surgery, so that the presently disclosed sphincteric system can be individually programmed to generate the minimum occlusive urethral pressure required by the patient's tissues to produce continence.

The occlusion cuff is also provided with a blood pulse transducer which is adapted to generate an electrical signal in response to a deformation caused by the patient's blood pulsing along the urethra. An electrical path is established between the transducer and an electronic pulse meter and/or a flashing light emitting diode and/or an audible alarm at the hyponometer. Thus, the physician may accurately and remotely monitor the patient's blood flow through the urethra so that the minimum occlusive pressure needed to produce continence can be determined, whereby to prevent the interruption of arteriovascular blood flow to the urethra and the possibility of ischemia, erosion, and the like that might otherwise be caused as a consequence of an over-inflation of the occlusion cuff and the application of excessive occlusive pressure to the urethra.

BRIEF DESCRIPTION OF THE DRAWINGS

FIG. 1 shows a unique hyponometer and the electro-fluidic interconnection of the hyponometer to a blood flow and occlusion pressure sensing sphincteric system which forms the present invention;

FIG. 2 is a detailed enlargement of an electrically conductive cell which forms part of the electro-fluidic interconnection of FIG. 1;

FIG. 4 shows a modified hyponometer for interconnection with the sphincteric system illustrated in FIG. 1;

DESCRIPTION OF THE PREFERRED EMBODIMENT

Figure 3:
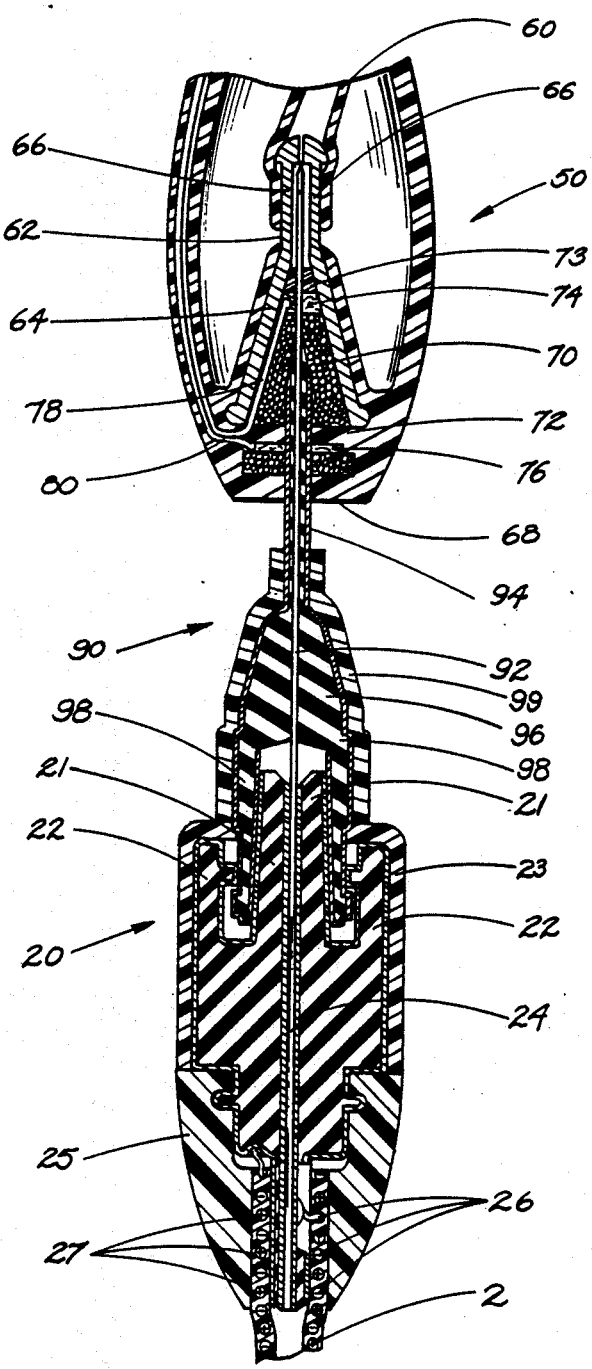
FIG. 3 shows a detailed enlargement, in cross-section, of the electro-fluidic interconnection of an electro-fluidic coupling, a dual conductor hypodermic needle, and a fluid pressure regulating and control chamber which forms part of the sphincteric system of FIG. 1.

The blood flow and occlusion pressure sensing sphincteric system which forms the present invention is now described while referring to the drawings. In FIG. 1, there is shown the electro-fluidic interconnection of a unique hyponometer 1, a dual conductor, hypodermic needle 90, a pressure regulating and fluid control system 50, and a hollow, inflatable occlusion cuff 30 surrounding a lumen 32 and having unique blood flow sensing and signaling means formed therein. By virtue of the present invention, and as will soon be described in greater detail, a measured supply of fluid can be variably and controllably delivered from hyponometer 1 and/or regulating and control system 50 to hollow occlusion cuff 30 for inflating the cuff and increasing the occlusive pressure being applied to the lumen 32 (e.g. the urethra) of an incontinent patient to selectively control the passage of material therethrough and enable the patient to be restored to urinary continence.

The occlusion pressure regulating and fluid control chamber 50 is initially described. It is to be noted that a regulating and control chamber similar to that illustrated in FIG. 1 was previously disclosed in U.S. Pat. No. 4,554,990 issue Apr. 29, 1986, the details of which are incorporated herein by reference. Therefore, only a brief description of the mechanical aspects of regulating and control chamber 50 is provided hereat. Chamber 50 is preferably formed from a biocompatible, elastomeric polymer material, such as silicone, polyurethane, or the like. Regulating and control chamber 50 includes a fluid filled reservoir 55 which communicates with occlusion cuff 30 by way of biocompatible (e.g. silicone) sphincter tubing 56. Fluid reservoir 55 is separated from sphincter tubing 56 by a plurality of flow control appendages 57 which extend in a normally closed condition across the proximal end of regulating and control chamber 50 at the interface of reservoir 55 with tubing 56 to prevent the flow of fluid therepast. Molded into the exterior of chamber 50 around the flow control appendages 57 is a pressure relief ring 58. Pressure relief ring 58 is of suitable size and shape to receive the thumb and index finger of a patient to perform a soon to be described function. During implant surgery, the regulating and control chamber 50 is preferably positioned at a palpable, loose skin area 59 (e.g. at the posterior superior aspect of the scrotum) so that chamber 50 is conveniently accessible to both the patient and/or physician in order that fluid can be transferred to inflate the hollow occlusion cuff 30 to thereby apply increased occlusive pressure to the urethra 32.

A physician control circuit shunt tube 60 extends through fluid reservoir 55 and between a needle receiving and directing insert 62 and the sphincter tubing 56. Insert 62 is preferably formed from a hard, sound, non-corrosive material, such a titanium alloy, or the like and is located in reservoir 55 and supported by an inwardly turned fold formed in the distal end of regulating and control chamber 50. Insert 62 comprises a hollow and generally conical base 64 at one end thereof and a hollow tubular portion 66 formed at the opposite end. In the assembled relationship, the conical base 64 of needle receiving and directing insert 62 functions as a hypodermic needle docking port and is located adjacent a subcutaneous physician locating terminal 68 formed at the extreme distal end of regulating and control chamber 50. The tubular end 66 of insert 62 is interconnected with physician control circuit shunt tube 60, as previously indicated, and has a small slit formed therein to permit fluid communication between insert 62 and tube 60. Tubular end 66 is of suitable size and configuration to form a safety stop for any needle that is located therein, whereby to limit the penetration of such needle and prevent damage to and possible leakage from physician control circuit shunt tube 60.

The interior of the needle receiving and directing insert 62 is filled with a dielectric material (e.g. gel) 70. The dielectric gel 70 is surrounded by the side walls of conical base 64, a polymer end cap 72 extending across the mouth of conical base 64, and a first electrically conductive cell 74 located at the interface of base 64 with insert tube portion 66. A polymer plug 73 is fit within insert 62 ahead of the first conductive cell 74. A second electrically conductive cell 76 is located within a pocket formed between the aforementioned polymer end cap 72 and the physician locating terminal 68 at the distal end of chamber 50. By way of example, and as is best shown in FIG. 2, each of the first and second electrically conductive cells 74 and 76 consists of silvers of tightly packed filings 77 of silver, or the like, sealed within a polymer envelope formed from silicone or other suitable dielectric elastomer material.

Conductive cells 74 and 76 are arranged in spaced axial alignment with one another so as to interconnect respective opposite polarity terminals of a blood flow transducer at occlusion cuff 30 with the hyponometer 1 by way of the soon-to-be described dual conductor, hypodermic needle 90. To this end, a first wire 78 is connected via tubing 56 between first conductive cell 74 and one terminal of the transducer at occlusion cuff 30. A second wire 80 is connected via tubing 56 between second conductive cell 76 and a second terminal of the transducer. Each of the wires 78 and 80 travels through a hollow channel 82 formed in a side wall of regulating and control chamber 50. Alternating turns of wires 78 and 80 spiral through the walls of tubing 56 from chamber 50 to occlusion cuff 30.

Like pressure regulating and fluid control chamber 50, occlusion cuff 30 is preferably formed from a biocompatible material, such as silicone, polyurethane, or the like. Occlusion cuff 30 includes a hollow fluid chamber 34 extending therearound which communicates with the fluid reservoir 55 of regulating and control chamber 50 by way of sphincter tubing 56. During implant surgery, occlusion cuff 30 is positioned by the physician so as to surround and articulate the bulbar or prostatic urethra 52 for occluding or relaxing the urethra to promote or obturate the movement of material therethrough.

Occlusion cuff 30 is interfaced with a transducer 36 that is advantageously adapted to sense blood flow through the patient's urethra and thereby provide an indication of dangerously high occlusive pressures being applied to the urethra which might obstruct circulatory blood flow. The transducer 36 preferably includes a piezoelectric film or strip which is embedded within an interior wall of occlusion cuff 30 adjacent urethra 32. As will be recognized by those skilled in the art, a piezoelectric transducer commonly comprises a crystalline molecularly aligned material that generates an electrical signal in response to the application of an external deformation. As previously disclosed, wires 78 and 80 are connected (via tubing 56) between conductive cells 74 and 76 and respective terminals of piezoelectric transducer 36. Accordingly, an electrical signal is transmitted over wires 78 and 80 each time that the crystalline material of piezoelectric transducer 36 is deformed (i.e. stressed) in response to pulses of blood through the patient's urethra 32. The application of excessive occlusive pressure to urethra 32 by overinflating occlusion cuff 30 will impede arteriovascular blood flow through axial and lateral blood vessels and cause a corresponding reduction in the amount of deformation of the transducer. Hence, the amplitude of the electrical signal generated by the piezoelectric transducer 36 is indicative of both the presence of blood flow and the occlusive pressure being applied to the patient's urethra. By virtue of the foregoing, a physician will be able to accurately monitor arteriovascular blood flow through the patient's urethra (at hyponometer 1, in a manner that will be hereinafter described), so that only the minimal occlusive pressure to achieve reliable, coaptive continence need be applied to a patient's urethra, whereby to advantageously reduce the possibility of ischemia, necrosis and erosion to the delicate tissues as a consequence of exceeding the maximum blood flow permitting level. Thus, and as an important result of the present invention, the long term safety and efficacy of a sphincteric bioimplant can be maximized by now being able to controllably generate extra lumenal occlusive pressures that are high enough to obstruct urine flow while still being low enough to permit blood flow.

The details of the dual conductor, hypodermic needle 90 for connecting hyponometer 1 to occlusion pressure regulating and fluid control chamber 50 are now described while referring concurrently to FIGS. 1 and 3 of the drawings. Hypodermic needle 90 includes inner and outer electrically conductive needle surfaces 92 and 94 and an insulator 96 located therebetween. Inner needle 92 is a conventional, non-coring, hollow Whitacre needle which may be silver plated to maximize electrical conductivity. Surrounding needle 92 is insulator 96 which is preferably injection molded from a suitable polymer material such as platable polysulfone, or the like. It may be desirable to form insulator 96 from upper and lower mold halves that are pressure-fit together around inner needle 92, such that the tip of needle 92 projects outwardly therefrom. As is best shown in FIG. 3, insulator 96 has a generally tubular distal end of solid cross-section (to be removably received by the needle receiving and directing insert 62) and a generally hollow, cylindrical proximal end 98 (to be releasably received by an electro-fluidic coupling). Outer needle surface 94 is formed by plating insulator 96 with a thin coating of electrically conductive material, such as silver, or the like, such that electrically conductive inner and outer needles 92 and 94 are coaxially aligned with and insulated from one another. The exterior of outer needle surface 94 is covered by a layer 99 of suitable insulating material.

In the interconnected relationship of FIGS. 1 and 3, the hypodermic needle 90 is shown removably inserted (i.e. forceably pushed) through physician locating terminal 68 of regulating and control chamber 50, such that the tip of inner needle 92 is received by the tube portion 66 of needle receiving and directing insert 62.

The electrically conductive inner needle 92 extends through the first conductive cell 74 and polymer plug 73 so as to come into electrical contact at cell 74 with the wire 78 (from one terminal of piezoelectrical transducer 36 of FIG. 1). The electrically conductive outer needle 94 extends through the second conductive cell 76 and end cap 72 so as to come into electrical contact at cell 76 with wire 80 (from the other terminal of piezoelectric transducer 36). In this manner, an electrical circuit is completed between transducer 36 and dual conductor, hypodermic needle 90 by way of wires 78 and 80 and conductive cells 74 and 76.

Hypodermic needle 90 is detached (i.e. forceably withdrawn) from regulating and control chamber 50 by pulling needle 90 outwardly from locating terminal 68 such that inner and outer needles 92 and 94 are disconnected from conductive cells 74 and 76. The polymer material of regulating and control chamber 50 is preferably characterized and/or augmented by a low durometer and high density so as to promote complete and fluid patent self-healing of any puncture wound formed in locating terminal 68, end cap 72 and end plug 73 to thereby avoid possible leakage as a consequence of inserting and withdrawing hypodermic needle 90.

An electro-fluidic coupling 20 for connecting hypodermic needle 90 to hyponometer 1 is now described. Projecting upwardly from a proximal end of coupling 20 are coextensively interconnected inner and outer cylinders 21 and 22 which are formed from a suitable insulating material and arranged in coaxial alignment with one another. Extending through coupling 20 at the interior of inner coupling cylinder 21 is a centrally disposed passageway 24. The exterior surfaces of inner and outer cylinders 21 and 22 and passageway 24 are coated with an electrically conductive material, such as silver, or the like (best shown in FIG. 3). The exterior of outer cylinder 22 is covered by a layer 23 of suitable insualting material.

At the distal end of coupling 20 is an electrical receptacle 25 which is also formed from an electrically insulating material and mated to the coextensive interconnection of inner and outer cylinders 21 and 22. The electrical receptacle end of coupling 20 is secured to one end of biocompatible hyponometer tubing 2 so as to electro-fluidically connect hyponometer 1 to hypodermic needle 90. That is, the conductive central passageway 24 is electrically connected to a first electrical wire 26, and the conductive inner and outer coupling cylinders 21 and 22 are electrically connected to a second electrical wire 27. Alternating turns of wires 26 and 27 spiral through the walls of tubing 2 from coupling 20 to hyponometer 1.

In the interconnected relationship of FIGS. 1 and 3, the cylindrical end 98 of dual conductor, hypodermic needle 90 is shown removably positioned between the inner and outer cylindrical ends 21 and 22 of coupling 20. Hypodermic needle 90 is rotated into interlocking engagement with coupling 20 in a well-known manner. The inner needle 92 of hypodermic needle 90 is received in electrical contact with and extends partially through the central passageway 24 of coupling 20, such that an electrical circuit is completed between inner needle 92 and wire 26 via the electrically conductive coating of passageway 24. Likewise, the outer needle 94 of hypodermic needle 90 is received in electrical contact with inner and outer coupling cylinders 21 and 22, such that an electrical circuit is completed between outer needle 94 and wire 27 via the electrically conductive coatings of cylinders 21 and 22.

Referring once again to FIG. 1 of the drawings, the hyponometer 1 is now described. Hyponometer 1 is a fluid filled cylinder which is adapted to dispense or withdraw a measured supply of fluid into tubing 2. Hyponometer 1 includes an anearobic manometer intrasphincter pressure gauge 4 which is adapted to provide the physician with an indication of the occlusive pressure, in centimeters of water, being applied to the patient's urethra 32 by occlusion cuff 30. That is, by virtue of the present invention, a fluid path is established between hyponometer 1 and the hollow chamber 34 of cuff 30 by way of hyponometer tubing 2, coupling passageway 24, hollowing needle 94, physician control tube 60 and sphincter tubing 56. Hyponometer 1 also includes an electrical blood flow (i.e. pulse) meter 6 which is adapted to provide the physician with an indication of each pulse of arteriovascular blood flow through the occluded urethra. That is, also by virtue of the present invention, an electrical circuit is established between blood flow meter 6 (e.g. a voltmeter) and the transducer 36 of occlusion cuff 30 by way of hyponometer wires 26 and 27, electro-fluidic coupling 20, inner and outer electrically conductive hypodermic needles 92 and 94, conductive cells 74 and 76 and sphincter wires 78 and 80.

Referring briefly to FIG. 4 of the drawings, a modified hyponometer 101 is shown. Hyponometer 101 is identical to the hyponometer 1 of FIG. 1 except that the blood flow meter 6 thereof is replaced by battery operated audible and visual signalling means 106 and 108. By way of example, the signalling means include a sound generator 106, known commercially by the trademark SONALERT and manufactured by Mallory Corporation, and a conventional high output light emitting diode 108, such as Part No. CND510 manufactured by General Instruments Corporation. By virtue of signalling means 106 and 108, the physician is provided with either an audible and/or visual signal corresponding to each pulse of arteriovascular blood flow through the urethra during and after the application of increased occlusive pressure to the urethra by means of inflating the occlusion cuff.

Figure 5:
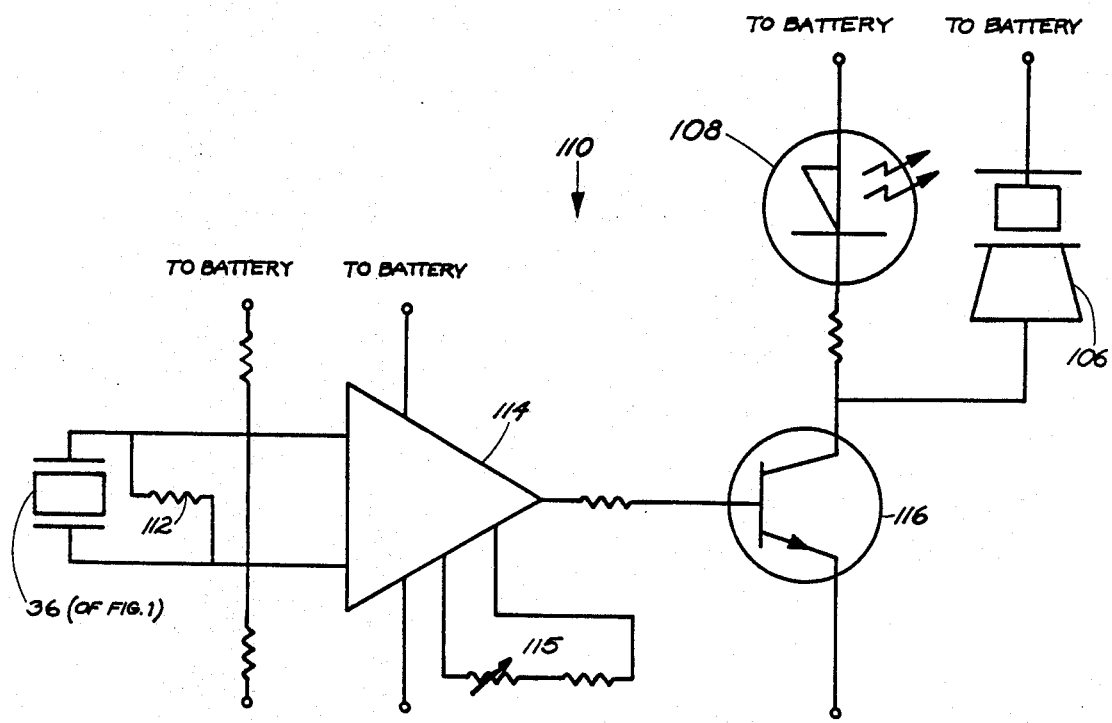
FIG. 5 represents a schematic of a circuit for electrically connecting a transducer of the present sphincteric system to a blood flow indicator at the hyponometer of FIG. 4.

An electrical circuit 110 by which to connect the piezoelectric transducer 36 of FIG. 1 to the audible and visual signalling means 106 and 108 of FIG. 4 is illustrated in FIG. 5 of the drawings. Transducer 36 is connected between a pair of input terminals of an operational amplifier 114, such as Part No. CA3140 manufactured by RCA Corporation. A noise damping resistor 112 is connected across transducer 36 to minimize the effect of any spurious signals being generated therefrom. A threshold voltage sensitivity circuit 115, including a potentiometer, or the like, is applied to another pair of input terminals of operational amplifier 114 to adjust the threshold voltage to which amplifier 114 is responsive, depending upon the selection of the piezoelectric transducing element.

The output terminal of operational amplifier 114 is connected through a current limiting resistor to the base of a conventional transistor 116, such as Part No. 2N222 available from a wide variety of manufacturers. The SONALERT audible signalling means 106 and th eight emitting diode visual signalling means 108 are respectively connected between a source of battery voltage and a common electrical junction formed with one (e.g. the collector) electrode of transistor 116. The other (e.g. the emitter) electrode of transistor 116 is connected to the source of battery voltage so as to float above ground.

In operation, operational amplifier 114 is responsive to an electrical signal, generated by transducer 36 and indicative of blood flow through the urethra, to drive transistor 116. A pulse at the output terminal of operational amplifier 114 will render transistor 116 conductive, whereby to momentarily energize both the SONALERT signalling means 106 and the light emitting diode signalling means 108 and provide audible and visual signals to the physician. In this manner, the physician receives redundant audible and visual indications of circulatory blood flow through the urethra so as to be able to reliably ascertain when such blood flow is compromised as a consequence of applying excessive occlusive pressure to the urethra.

Referring once again to FIG. 1 of the drawings and located at the bottom of hyponometer 1 is a rotatable vernier infusion/exfusion dial 8. The rotation of dial 8 causes a corresponding movement of an internal piston 10 through the interior of hyponometer 1 to force fluid outwardly therefrom or inwardly thereinto by way of tubing 2. A series of volume indicator lines 12 is printed on a surface of hyponometer 1. Lines 12 correspond with each of a plurality of particular positions of piston 10, so as to provide an indication, in cubic centimeters of water, of the volume of fluid dispensed from or drawn into hyponometer 1 as piston 10 is moved therethrough. A fluid infusion port 14 communicates with the interior of hyponometer 1 so that the hyponometer may be more rapidly infused with an additional supply of fluid by means of a conventional syringe 16 (shown in phantom). A back pressure release button 18 is also associated with hyponometer 1 to permit constant pressure readout of the anaerobic manomeric pressure guage 4. Depressing button 18 opens an internal check valve (not shown) to allow fluid to flow back into hyponometer 1 through tubing 2, whereby to increase the fluid volume contained within the hyponometer.

In operation, in order to achieve urinary continence, the patient inflates the hollow chamber 34 of occlusion cuff 30 by manually compressing reservoir 55 so as to reduce the volume thereof. The compression of reservoir 55 forces fluid outwardly therefrom so as to separate flow control appendages 57 and permit the movement of fluid through sphincter tubing 56 and, subsequently, to the hollow chamber 34 of occlusion cuff 30. When the compression of reservoir 55 is completed, the natural tendency of the normally closed flow control appendages appendages to again engage one another so as to prevent the movement of fluid therepast.

Occasionally, however, the patient may experience a return of natural continence such as may occur during the hours of sleep. A reduction in fluidic head pressure on the urethra (coupled with any remaining natural sphincteric function) may contribute to keeping the patient continent while in the supine sleeping position. At such times of temporarily-returned continence, it may periodically become advantageous to reduce the occlusive pressures being applied to the patient's urethra 32 to minimize the possibility of ischemia, atrophy, necrosis and erosion. Accordingly, the pressure relief ring 58 may be manually activated, whereby to shrink chamber 34 and thereby maximize circulatory blood flow through the urethra 32. More particularly, the pressure relief ring 58 is grasped between the patient's thumb and index finger so that equal and opposite omniradial forces are applied thereto. Such omniradial forces are transmitted to the flow control appendages 57 to once again open appendages 57 and permit the suction of fluid therethrough from an inflated occlusion cuff chamber 34 back to the reservoir 55. Hence, the inflated chamber 34 of occlusion cuff 2 will shrink to reduce the occlusive pressures being applied to the patient's urethra and thereby minimize interference with circulatory blood flow.

However, in the event that the patient is unable to successfully achieve post-surgical continence by expanding hollow chamber 34 of occlusion cuff 30, means are advantageously provided to the physician by which to variably increase the occlusive pressure generated by occlusion cuff 30 without the need for additional surgery. Thus, the physician alone may set the maximum total occlusive pressure limit to be generated by occlusion cuff 30. More particularly, the physician may continuously and accurately increase or decrease occlusive pressure being applied to the patient's urethra by inserting the dual conductor, hypodermic needle 90 through the physician locating terminal 68 of pressure regulating and fluid control chamber 50, as previously disclosed. In this manner, the physician control circuit shunt tube 60 can be percutaneously infused with a minimum volume of fluid necessary to inflate chamber 34 until minimum pressure continence is provided. That is, chamber 34 may be percutaneously infused (or drained) with a carefully metered supply of fluid from or to hyponometer 1 via the previously described fluid path therebetween. Moreover, by inserting a syringe 16 through infusion port 14 of hyponometer 1, an additional fluid supply is available to further inflate chamber 34 and increase the occlusive pressure needed to produce continence or to remove excess fluid and thereby restore compromised patient blood flow.

By virture of hyponometer 1, coupling 20 and dual conductor, hypodermic needle 90, a redundant occlusion pressure increasing or decreasing means is available without additional surgery in the event that either the maximum force generated from the compression of reservoir 55 and the corresponding inflation of occlusion cuff chamber 34 is insufficient, in itself, to achieve coaptation or the increased occlusive pressure is overly high so as to compromise blood flow. Because the physician may continuously adjust the total occlusive pressure physician may continuously adjust the total occlusive pressure after surgery, absolute minimum continence-producing pressures may be percutaneously set after internal tissue conditions have normalized so that the sphincter system of the present invention can be individually programmed to the physical tissue property requirements of the patient. What is more, the physician is provided with an accurate, readily available indication of the patient's blood flow through the urethra via the previously described electrical path between piezoelectric transducer 36 and hyponometers 1 and 101. Thus, the physician will be able to reliably determine the minimal occlusive pressure needed to achieve coaptation and assure that such pressure is also low enough to prevent strangulation of delicate urethral tissue by interruption of arteriovascular blood flow therethrough.

It will be apparent that while a preferred embodiment of the invention has been shown and described, various modifications and changes may be made without departing from the true spirit and scope of the invention. For example, the preferred location for positioning occlusion cuff 30 in order to occlude and relax the patient's urethra is to surround the bulbous urethral portion of the corpus spongiosum. However, it is to be understood that the lumen which may be surrounded by occlusion cuff 30 may also be an intestine, the esophagus, an artery, a vein, or the vas deferins.

Having set forth a preferred embodiment of the invention, What is claimed is:

1. A blood flow and occlusion pressure sensing sphincter system having a hollow, infatable occlusion cuff to be located around the urethra of an incontinent patient for occluding and relaxing the urethra to enable the patient to be restored to continence, said sphincter system also comprising:

fluid source means interconnected with said occlusion cuff to supply fluid thereto, whereby to inflate said cuff and apply occlusive pressure to the urethra for achieving coaptation;

transducer means to provide an output signal in response to the patient's blood flow through the urethra when said cuff is inflated and the urethra is occluded;

indicator means interconnected with said transducer means to receive the output signal therefrom for providing an indication when excessive occlusive pressure is applied to the urethra so as to interrupt the flow of blood therethrough; and electro-fluidic path means including first and second electrically conductive portions, said first and second portions being electrically connected between respective ones of a pair of opposite polarity terminals of said transducer means and corresponding terminals of said indicator means for transmitting the output signal of said transducer means to said indicator means, said first portion being of hollow, tubular construction and interconnected between said fluid source means and said occlusion cuff for infusing said cuff with fluid from said source means.

2. The sphincter system recited in claim 1, wherein said transducer means includes a piezoelectric sensing element.

3. The sphincter system recited in claim 1, wherein said indicator means is a voltmeter.

4. The sphincter system recited in claim 1, wherein said indicator means is a light emitting diode.

5. The sphincter system recited in claim 1, wherein said indicator means includes audible signalling means.

6. The sphincter system recited in claim 1, wherein said fluid source means includes a compressible fluid reservoir interconnected with said inflatable occlusion cuff, said reservoir being located at a subcutaneously accessible, loose skin area of the patient so that said reservoir can be manually compressed to force a supply of fluid outwardly therefrom for delivery to said occlusion cuff to inflate said cuff and apply continence-producing occlusive pressure to the urethra.

7. The sphincter system recited in claim 1, wherein said fluid source means includes a remote hyponometer interconnected with said occlusion cuff so that fluid can be percutaneously infused or removed from said hyponometer to said occlusion cuff by way of the hollow, tubular portion of said electro-fluidic path means to either inflate or deflate said cuff and thereby apply increased or decreased occlusive pressure to the urethra.

8. The sphincter system recited in claim 7, wherein said indicator means is located at said hyponometer.

9. The sphincter system recited in claim 7, further comprising occlusion pressure indicating means connected to said occlusion cuff by way of said electro-fluidic path means for providing an indication of the occlusive pressure being applied to the patient's urethra, said occlusion pressure indicating means located at said hyponometer.

10. The sphincter system recited in claim 7, wherein said electro-fluidic path means comprises a hypodermic needle, the first and second portions of said electro-fluidic path means being formed by inner and outer electrically conductive needle portions coaxially aligned with one another and separated by an insulator.

11. The sphincter system recited in claim 10, wherein said electro-fluidic path means also comprises a hypodermic needle guiding port for removably receiving said hypodermic needle therewithin and first and second electrically conductive surfaces located at opposite ends of said port and being insulated from one another, said first and second conductive surfaces respectively connected to different ones of said pair of terminals at said transducer means, said inner hypodermic needle portion being moved into electrical contact with said first conductive surface for connection to one of said transducer terminals and said outer hypodermic needle portion being moved into electrical contact with said second conductive surface for connection to the other of said transducer terminals when said hypodermic needle is inserted within said guiding port.

12. The sphincter system recited in claim 10, wherein said inner hypodermic needle portion is interconnected between said hyponometer and said occlusion cuff.

13. The sphincter system recited in claim 1, wherein said transducer means has a layer of piezoelectric material located within the interior of said occlusion cuff adjacent the urethra.

14. A sphincteric system including a hollow, inflatable occlusion cuff to be located around the urethra of an incontinent patient for occluding and relaxing the urethra to enable the patient to achieve continence, said sphincteric system comprising:
   hyponometer means to be interconnected with said occlusion cuff so that said cuff can be percutaneously infused with or exfused of a measured supply of fluid, whereby to inflate or deflate said cuff and regulate occlusive pressure to the urethra;
   transducer means located at said occlusion cuff to provide an output signal in response to the patient's blood flow through the urethra when said cuff is inflated and said urethra is occluded;
   indicator means located at said hyponometer means and interconnected with said transducer means to receive the output signal therefrom and provide an indication when excessive occlusive pressure is applied to the urethra so as to interrupt the flow of blood therethrough; and
   electro-fluidic path means located between said hyponometer means and said occlusion cuff and having a fluid circuit to convey fluid from said hyponometer means to said occlusion cuff and an electrical circuit to transmit the output signal of said transducer means to said indicator means at said hyponometer means.

15. The sphincteric system recited in claim 14, wherein said transducer means includes a piezoelectric sensing element.

16. The sphincteric system recited in claim 14, wherein said indicator means is a voltmeter.

17. The sphincteric system recited in claim 14, wherein said indicator means is a light emitting diode.

18. The sphincteric system recited in claim 14, wherein said indicator means includes audible signalling means.

19. The sphincteric system recited in claim 14, further comprising compressible fluid reservoir means interconnected with said inflatable occlusion cuff, said reservoir means being located at a subcutaneously accessible, loose skin area of the patient so that said reservoir means can be manually compressed to force a supply of fluid outwardly therefrom for delivery to said occlusion cuff to inflate said cuff and apply additional occlusive pressure to the urethra.

20. The sphincteric system recited in claim 14, wherein said electro-fluidic path means includes a dual conductor, hypodermic needle having inner and outer electrically conductive needle portions coaxially aligned with one another and separated by an insulator;
   said inner and outer needle portions being detachably and electrically connected between respective ones of a pair of opposite polarity terminals of said transducer means and corresponding terminals of said indicator means for transmitting the output signal from said transducer means to said indicator means; and
   said inner needle portion being of hollow construction to convey fluid from said hyponometer means to said occlusion cuff.

21. The sphincteric system recited in claim 20, further comprising hypodermic needle port means for removably receiving said hypodermic needle therewithin and first and second electrically conductive surfaces located at opposite ends of said port means and being insulated from one another, said first and second conductive surfaces respectively connected to different ones of said pair of terminals at said transducer means, said inner hypodermic needle portion being moved into electrical contact with said first conductive surface for connection to one of said transducer terminals and said outer hypodermic needle portion being moved into electrical contact with said second conductive surface for connection to the other of said transducer terminals when said hypodermic needle is inserted within said port means.

22. A sphincteric system including an inflatable occlusion cuff to be located around the urethra of an incontinent patient for occluding and relaxing the urethra to enable the patient to achieve continence, said system comprising:
   fluid source means interconnected with said occlusion cuff to supply fluid thereto for inflating said cuff and applying occlusive pressure to the urethra for occluding the urethra;
   hyponometer means containing a supply of fluid and interconnected with said occlusion cuff to selectively supply additional fluid thereto for increasing the occlusive pressure to the urethra until coaptive continence is achieved;
   transducer means located at said occlusion cuff to provide an output signal in response to the patient's blood flow through the urethra when said cuff is inflated and the urethra is occluded;
   indicator means interconnected with said transducer means to receive the output signal therefrom for providing an indication when excessive occlusive pressure is applied to the urethra so as to interrupt the blood flow therethrough; and electro-fluidic path means having first and second electrically conductive portions to be electrically connected between respective terminals of said transducer means and corresponding terminals of said indicator means for transmitting the output signal of said transducer means to said indicator means, the first portion of said electro-fluidic path means being of hollow, tubular construction and interconnected between said hyponometer means and said occlusion cuff to convey fluid therebetween.

23. The sphincteric system recited in claim 22, wherein said electro-fluidic path means comprises a hypodermic needle having inner and outer electrically conductive, cylindrical needle portions coaxially aligned with one another and separated by an insulator, the inner and outer portions of said hypodermic needle corresponding to the first and second portions of said electro-fluidic path means.

24. The sphincteric system recited in claim 22, wherein said indicator means is located at said hyponometer means.

25. The sphincteric system recited in claim 22, wherein said fluid source means comprises a compressible fluid reservoir communicating with said occlusion cuff by way of a hollow tubing section, the first portion of said electro-fluidic path means also communicating with said occlusion cuff by way of said hollow tubing section.

* * * * *